United States Patent [19]
Gautsch et al.

[11] Patent Number: 6,027,750
[45] Date of Patent: Feb. 22, 2000

[54] SYSTEMS AND METHODS FOR THE RAPID ISOLATION OF NUCLEIC ACIDS

[76] Inventors: James Gautsch, 520 S. Granados, Solana Beach, Calif. 92075; Mark Brolaski, 665 Riqueza St., Encinitas, Calif. 92024

[21] Appl. No.: 08/591,038

[22] Filed: Jan. 25, 1996

Related U.S. Application Data

[62] Division of application No. 08/309,926, Sep. 21, 1994, abandoned, which is a division of application No. 07/962,418, Oct. 16, 1992, abandoned, which is a continuation-in-part of application No. 07/267,530, Nov. 4, 1988, abandoned, which is a continuation-in-part of application No. 06/903,481, Sep. 4, 1986, abandoned.

[51] Int. Cl.⁷ ............... A61K 9/14; C07H 21/00; C07H 21/02; C07H 21/04
[52] U.S. Cl. ............ 424/489; 536/25.4; 210/27; 210/28; 210/29; 210/40
[58] Field of Search .................. 436/526, 525, 436/527, 808; 435/6, 404, 253.6, 810; 935/77–78; 424/451, 484, 489; 536/25.4, 24–41; 210/27, 28, 29, 40

[56] References Cited

U.S. PATENT DOCUMENTS

| | | | |
|---|---|---|---|
| 4,116,828 | 9/1978 | Sawyer, Jr. | 210/27 |
| 4,483,920 | 11/1984 | Gillespie et al. | |
| 4,672,040 | 6/1987 | Josephson | 436/526 |
| 5,658,790 | 8/1997 | Gautsch | 435/404 |

OTHER PUBLICATIONS

Aguilar–Cordova et al. "Rapid Isolation of sunstrate Quality plasmid DNA without CsCl–Dye Density Gradients". Bio-Techniques. vol. 9, No. 5, pp. 538–540, 1990.

Gamper et al, Laboratory Methods: "Purification of Circular DNA Using Benzoylated Naphthoylated DEAE–Cellulose," *DNA*, 4:157–164 (1985).

Yang et al, "Elution of DNA from Agarose Gels After Electrophoresis," *Meth. Enzol.*, 68:176–182 (1979).

Vogelstein et al, "Preparative and Analytical Purification of DNA fro Agarose," *Proc. Natl. Acad. Sci, USA*, 7:615–619 (1979).

Birnboim, "A Rapid Alkaline Extraction Method for the Isolation of Plasmid DNA," *Meth. Enzol.*, 100:243–255 (1983).

Mizutani, "Adsorption Chromotography of Ribonucleic Acids on Controlled–Pore Glass," *J. Chrom.*, 262:441–445 (1983).

Marko et al, "A Procedure for the Large–Scale Isolation of Highly Purified Plasmid DNA Using Alkaline Extraction and Binding to Glass Powder," *Anal. Biochem.*, 121:382–387 (1982).

Chen et al, "Recovery of DNA Segments from Agarose Gels," *Anal. Biochem.*, 101:339–341 (1980).

*Primary Examiner*—Lynette R. F. Smith
*Assistant Examiner*—Datquan Lee
*Attorney, Agent, or Firm*—Thomas Fitting

[57] ABSTRACT

The present invention contemplates a system for rapidly isolating nucleic acids. The system comprises an insoluble silica matrix and a buffered aqueous salt solution containing salt at a concentration of at least 3 molar and a buffering agent at a concentration sufficient to provide a buffering capacity corresponding to that which either tris (hydroxymethyl)aminomethane or phosphate ion at a concentration of 0.1 to 1 molar would provide in the solution. Methods of using the system are also contemplated.

18 Claims, 5 Drawing Sheets

SYSTEMS AND METHODS FOR THE RAPID ISOLATION OF NUCLEIC ACIDS

CROSS-REFERENCE TO RELATED APPLICATION

This is a division of application Ser. No. 08/309,926, filed Sep. 21, 1994, now abandoned which is a division of application Ser. No. 07/962,418, filed Oct. 16, 1992, now abandoned, which is a continuation-in-part application of application Ser. No. 07/267,530, filed Nov. 4, 1988, now abandoned, which is a continuation-in-part of application Ser. No. 06/903,481, filed Sep. 4, 1986, now abandoned, the disclosures of which are hereby incorporated by reference.

TECHNICAL FIELD

The present invention relates to methods and systems for rapidly isolating nucleic acids. More particularly, this invention contemplates systems and methods for isolating plasmid DNA from cell lysates and DNA from agarose gels.

BACKGROUND

The isolation of preparative amounts of biologically active nucleic acid molecules has been a vexing problem in molecular biology. This is especially the case with regard to isolation of DNA for use in recombinant methodologies where it is required to be in sufficiently pure form to be digestible by restriction endonucleases, to be a good substrate for polymerases and topoisomerases, and to be suitable for use as a transfection or transformation agent.

Over the years, many methods have been developed to isolate nucleic acid molecules. However, those methods are typically tedious, require a high level of skill to perform, take extended periods of time to accomplish, require the processing of relatively large volumes of materials and often give variable results. In addition, most of the isolation techniques reported are costly in terms of equipment and materials. See, Gamper et al., *DNA*, 4:157–164 (1985); Yang et al., *Meth. Enzol.*, 68:176–182 (1979); and Vogelstein et al., *Proc. Natl. Acad. Sci. USA*, 7:615–619 (1979).

To date, the art has applied several different technologies to the problem of preparing nucleic acids in quantities and purities sufficient for use in recombinant methodologies. Classically, the final step in the isolation of plasmid DNA is a cesium chloride-ethidium dye isopycnic gradient ultracentrifugation through a neutral or alkaline density gradient, gel electrophoresis, high-pressure liquid chromatography through RPC-5, alkaline extraction and column chromatography on methylated albumin kieselguhr, hydroxyapatite, or benzoylated naphthoylated DEAE-cellulose. See Gamper et al., *DNA*, 4:157–164 (1985); Yang et al., *Meth. Enzol.* 68:176–182 1979); Birnboim, *Meth. Enzol.*, 100: 243–255 (1983); *Mizutani, J. Chrom.*, 262:441–445 (1983); and the references cited therein.

Of particular interest to the present invention are methods wherein the nucleic acid to be isolated is adsorbed onto an insoluble silica matrix, e.g., particulate glass. While there are several reports of using the binding of nucleic acids to particulate glass as an isolation means, the physio-chemical mechanism(s) responsible for the binding phenomenon and the conditions under which it occurs are poorly characterized. Advances in the art have therefore proceeded on an empirical basis.

The use of adsorption onto glass as a means for isolating nucleic acids is based on the observation that both DNA and RNA bind to glass in highly concentrated aqueous salt solutions, i.e., salt concentrations of at least about 3 molar, and can be eluted therefrom by lowering the salt (ionic) concentration. While the pH value of the salt solution appears to have some effect on the adsorption process, that effect has not been characterized.

There have been several reports on the use of the glass-adsorption technique to isolate DNA from agarose gels. In each case, the salt solutions used to mediate the binding of the nucleic acids to the glass contained the buffering agent tris (hydroxymethyl) aminomethane at a concentration of less than 50 millimolar. Those solutions therefore had a low buffering capacity. See, Mizutani, *J. Col. Inter. Sci.*, 93:270–273 (1983); Mizutani, *J. Chrom.*, 262:441–445 (1983); Marko et al., *Anal. Biochem.*, 121:382–387 (1982); Chen et al., *Anal. Biochem.*, 101:339–341 (1980); Vogelstein et al., *Proc. Natl. Acad. Sci. USA*, 76:615–619 (1979); and Yang et al., *Meth. Enzol.*, 68:176–182 (1979).

None of the previously reported methods of isolating nucleic acids by glass-adsorption has gained widespread acceptance by those skilled in the art of recombinant DNA technology. This is probably due to the inability of those methods to consistently separate DNA from sample contaminants such as RNA, protein and agarose. For instance, Marko et al., supra, reported that the buffered salt solution used to mediate DNA binding to glass was required to contain the chelating agent cyclohexanediamine tetraacetate (CDTA) in order to prevent binding of tRNA to glass and co-purification of the tRNA with the plasmid DNA.

From the foregoing it can be seen that there has been a long felt need by those practicing recombinant DNA technology for a reliable, rapid method for isolating nucleic acid molecules.

BRIEF SUMMARY OF THE INVENTION

The present invention contemplates systems and methods for isolating nucleic acids. The systems and methods take advantage of solutions to the problems, discovered by the inventor, of insufficient buffering capacity and excessive glass particle heterogeneity.

In addition, the novel systems approach described herein permits a significant reduction in the level of skill and time required to produce isolated DNA.

In one embodiment, the present invention contemplates a system, in kit form, for isolating plasmid DNA from an aqueous sample. The system comprises, in separate containers, particulate glass and a buffered aqueous salt solution having a pH value in the range of 7 to 8. The solution contains:
 a) a salt at a concentration of at least 3 molar, and
 b) a buffering agent at a concentration sufficient to provide a buffering capacity corresponding to that 0.1 to 1 molar tris(hydroxymethyl)aminomethane or 0.1 to 1 molar phosphate ion would provide in solution.

Another aspect of the present invention is a system, in kit form, for isolating plasmid DNA from a sample. The system comprises, in separate containers:
 a) particulate glass; and
 b) a buffered aqueous salt solution having a pH value in the range of 7.2–7.8. The solution consists essentially of:
  i) 2M NaI,
  ii) 2.6M KBr, and
  iii) 0.66M tris(hydroxymethyl)aminomethane.

Also contemplated is a system, in kit form, for isolating nucleic acid molecules. The system comprises a composition comprising particulate glass having a sedimentation rate through still water at unit gravity in the range of about 0.001 to about 1.0 cm/min.

A further aspect of this invention is a system, in kit form, for isolating DNA from an aqueous sample. The system comprises, in separate containers, particulate glass and a buffered salt admixture which upon dissolution in a predetermined amount of distilled water provides a solution having a pH value in the range of 7 to 8. The buffered salt admixture contains:

a) a salt in an amount sufficient to provide a concentration of at least 3 molar upon said dissolution, and b) a buffering agent at a concentration sufficient to provide a buffering capacity corresponding to that provided by 0.1 to 1 molar aqueous tris(hydroxymethyl) aminomethane or 0.1 to 1 molar aqueous phosphate ion.

A further embodiment of this invention is a method for isolating plasmid DNA from an aqueous sample. The method comprises the steps of:

a) forming a binding reaction admixture by admixing said sample with an insoluble silica matrix and a buffered aqueous salt solution having a pH value in the range of 7 to 8, said solution containing i) a salt at a concentration of at least 3 molar, and ii) a buffering agent at a concentration sufficient to provide a buffering capacity corresponding to that which 0.1 to 1 molar tris (hydroxymethyl)aminomethane or 0.1 to 1 molar sodium phosphate would provide in said solution;

b) maintaining said binding reaction admixture for a time period sufficient for said DNA to bind to said matrix to form an insoluble DNA-matrix complex and a remaining admixture;

c) separating said remaining admixture and said complex to form an isolated complex; and d) recovering said DNA from said isolated complex to form isolated plasmid DNA.

The present invention also contemplates a method for isolating DNA from an agarose gel sample. The method comprises the steps of:

a) forming a gel-dissolving reaction admixture by admixing said sample with a buffered aqueous chaotropic salt solution having a pH value in the range of 7 to 8, said solution containing i) a chaotropic salt at a concentration of at least 3 molar, and ii) a buffering agent at a concentration sufficient to provide a buffering capacity corresponding to that which 0.1 to 1 molar tris (hydroxymethyl)aminomethane or 0.1 to 1 molar phosphate would provide in said solution;

b) maintaining said gel-dissolving reaction admixture at a temperature of about 45 to about 65 degrees C. for a time period sufficient for said gel sample to dissolve to form a dissolved sample;

c) admixing said dissolved sample with an insoluble silica matrix to form a binding reaction admixture;

d) maintaining said binding reaction admixture for a time period sufficient for said DNA present in said sample to bind to said matrix to form a solution containing dissolved agarose and an insoluble DNA-matrix complex;

e) separating said complex from said dissolved agarose to form an isolated complex; and f) recovering said DNA from said isolated complex to form isolated DNA.

In another embodiment, the invention describes a dry-concentrate culture medium composition packaged in unit dose form comprising an amount of cell culture medium in dry-concentrate form sufficient to prepare a preselected amount of culture medium. Preferably, the unit dose packaging is in the form of a capsule containing the dry culture medium. In a related embodiment, the packaging is comprised of a dissolvable material.

BRIEF DESCRIPTION OF THE DRAWINGS

In the drawings, forming a portion of this disclosure:

FIGS. 1–4 illustrate electron micrographs of the particulate glass fractions prepared in Example 1. Each sample is shown in two magnifications in an upper and lower panel. A white bar line in the lower right corner of each panel indicates the relative size of the glass particles in each sample.

DETAILED DESCRIPTION OF THE INVENTION

A. Systems For-Isolatinc Nucleic Acids

Figure 1A:
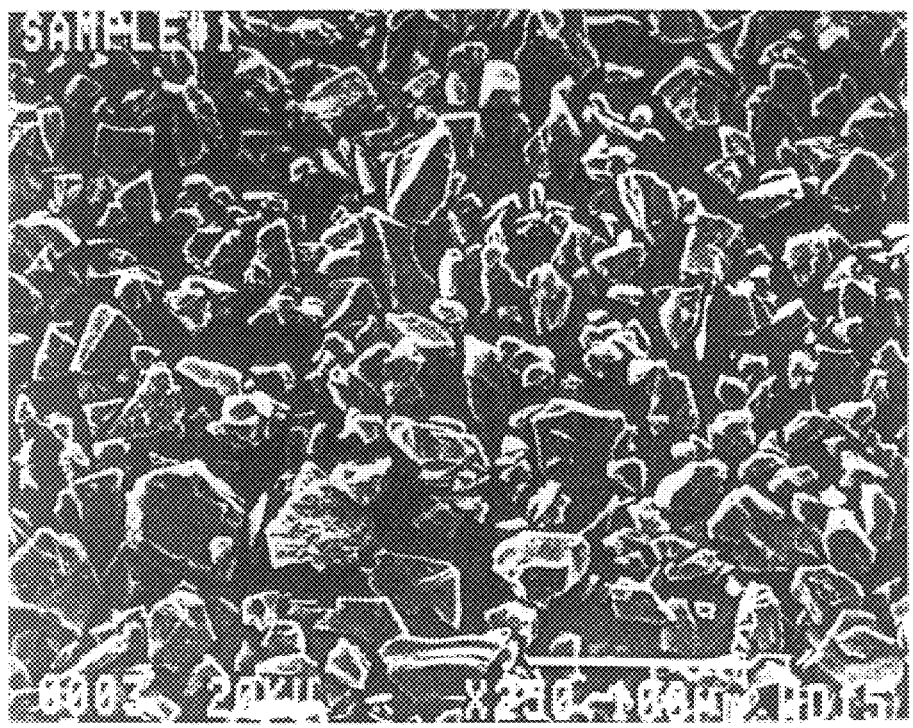
FIGS. 1A and 1B depicts fraction 1 at magnifications of ×250 and ×500, and includes a bar line of 100 µm and 100 µm, in the upper and lower panels, respectively.
Figure 1B:
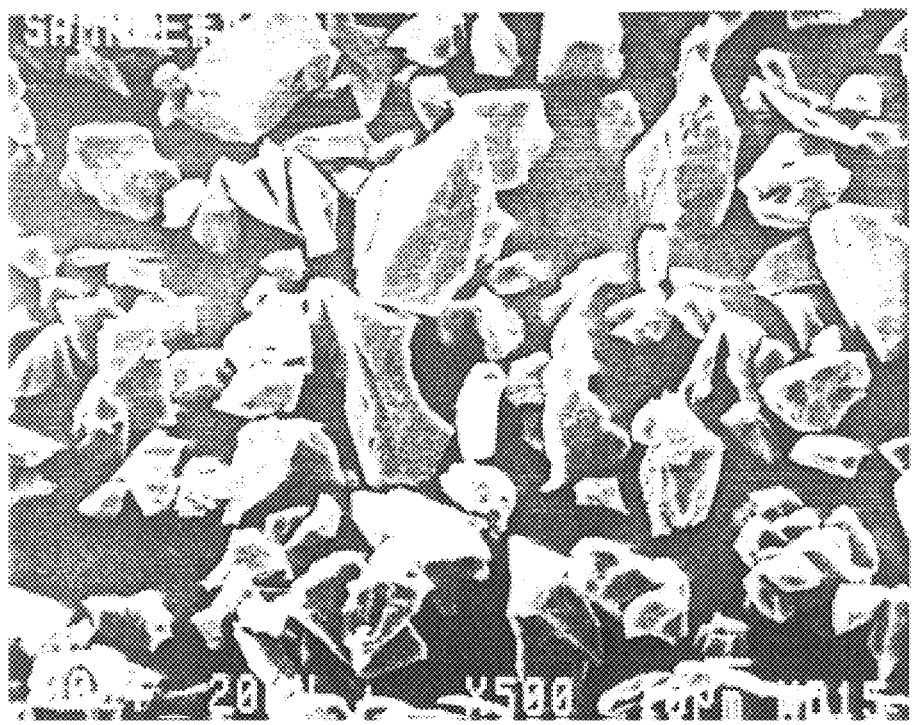
Figure 2A:
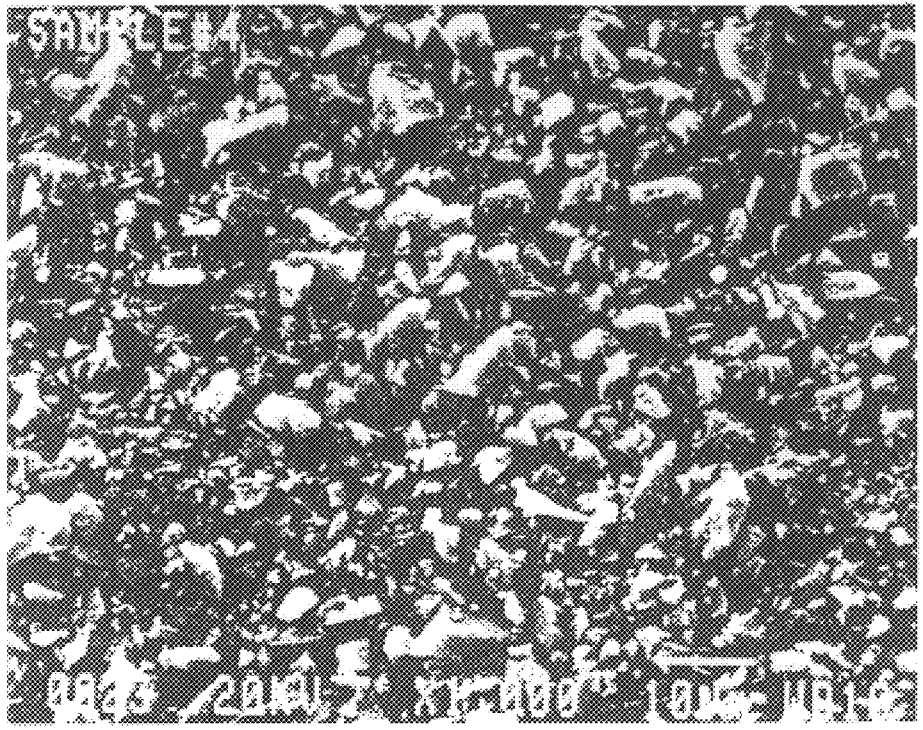
FIGS. 2A and 2B depicts fraction 4 at magnifications of ×1,000 and ×2,000, and includes a bar line of 10 µm and 10 µm, in the upper and lower panels, respectively.
Figure 2B:
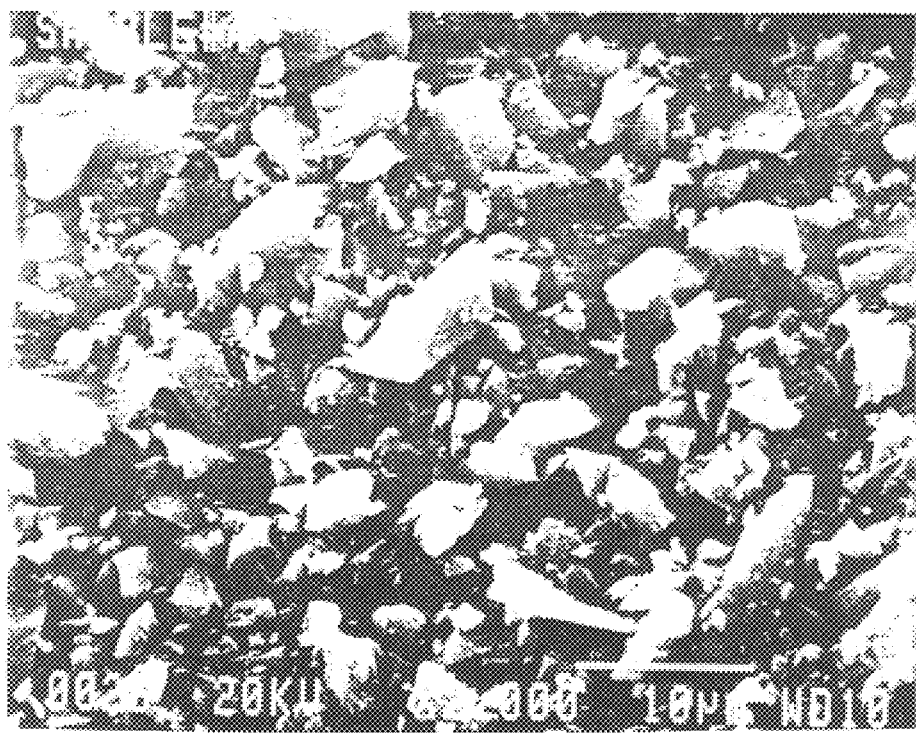
Figure 3A:
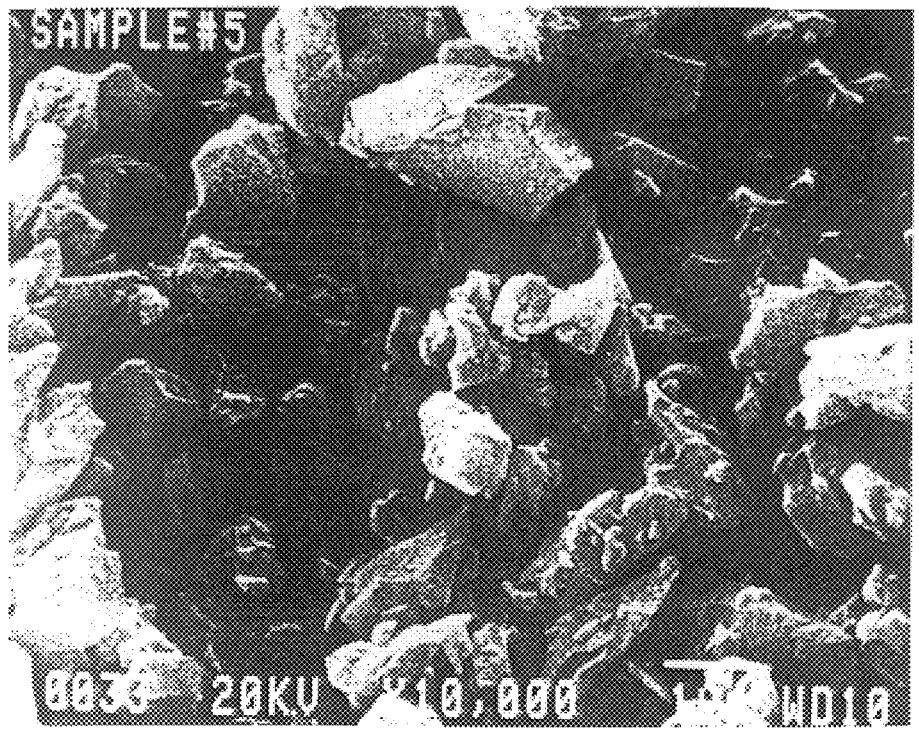
FIGS. 3A and 3B depicts fraction 5 at magnifications of ×10,000 and ×20,000, and includes a bar line of 1 µm and 1µ, in the upper and lower panels, respectively.
Figure 3B:
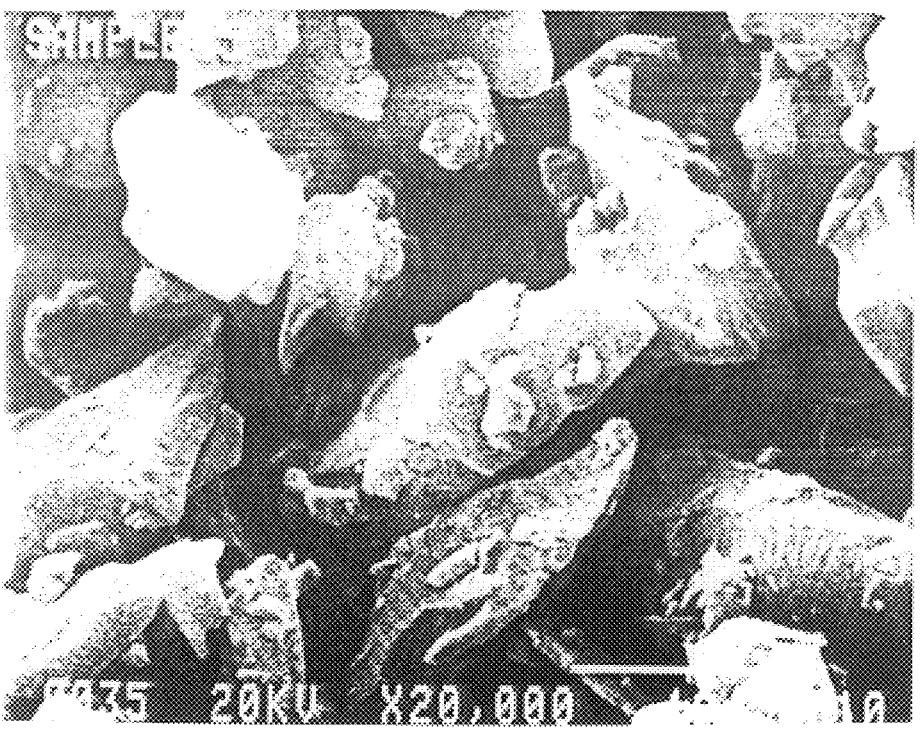
Figure 4A:
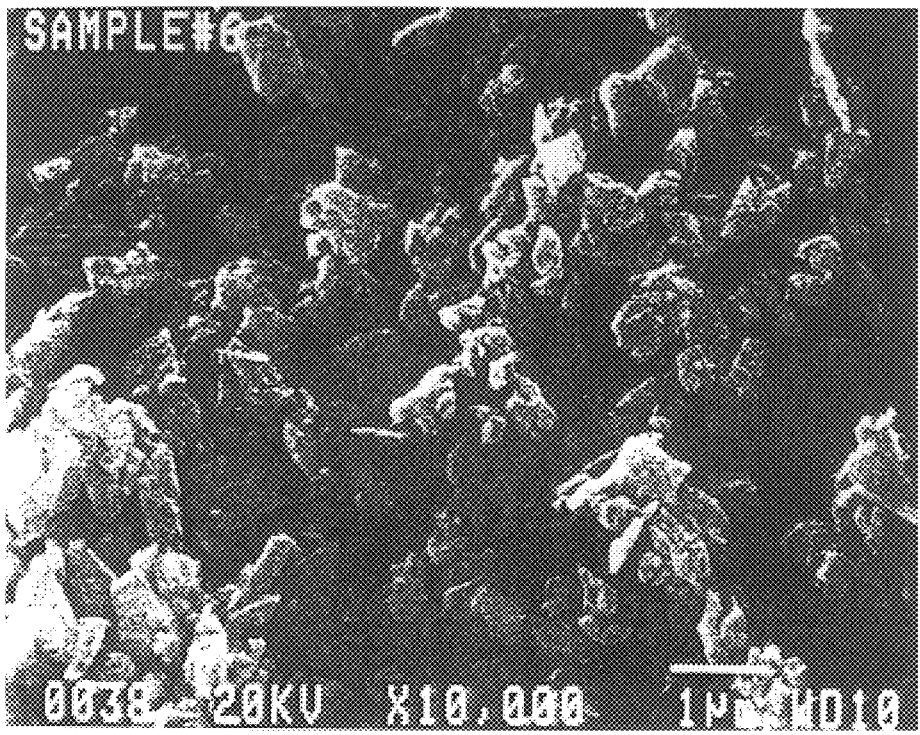
FIGS. 4A and 4B depicts fraction 6 at magnifications of ×10,000 and ×35,000, and includes a bar line of 1 µm and 1 µm, in the upper and lower panels, respectively.
Figure 4B:
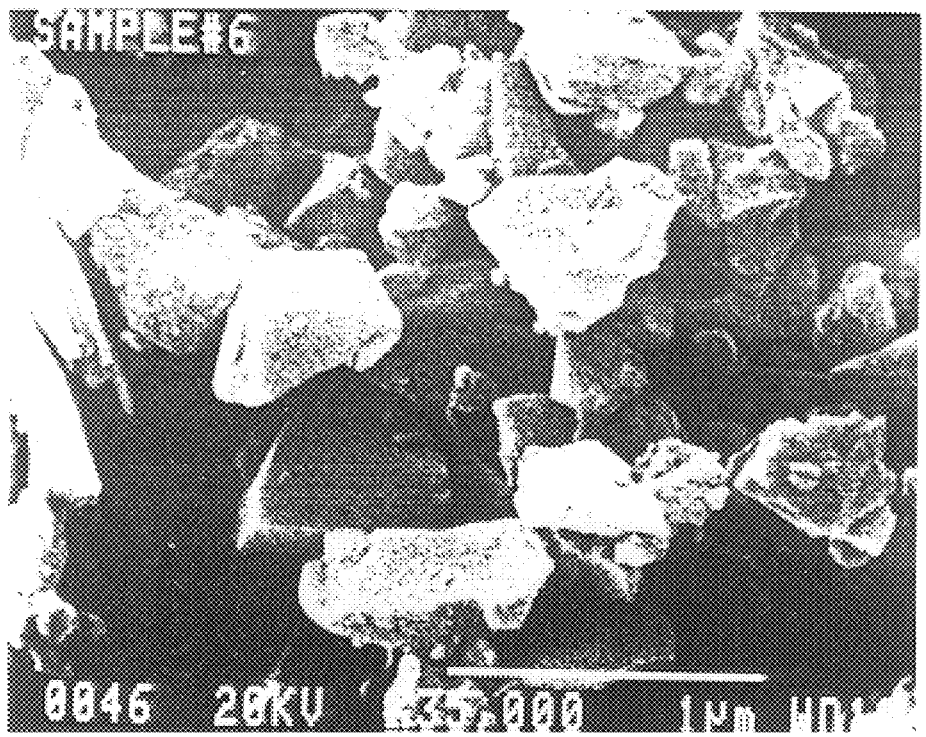

The present invention contemplates a system, in kit form, for isolating nucleic acid molecules. The system includes, as a separately packaged component, an insoluble silica matrix, preferably particulate glass, in an amount sufficient to bind at least 2–3 micrograms (µg) of nucleic acid. In preferred embodiments, the particle size of the glass is in the range of about 0.001 to about 1.0 centimeters/minute (cm/min), more preferably about 0.1 to 0.01 cm/min determined by sedimentation rate through water at unit gravity.

The size of the glass particles can also be described in terms of an average longest-diameter and/or range thereof. Thus, in preferred embodiments the average glass particle size is about 2 to 8 microns in a composition having a glass particle size range of about 0.8 to 30 microns. More preferably, the average glass particle size is about 8 microns in a composition having a glass particle size range of about 1.5 to 30 microns.

In addition to an insoluble silica matrix, a preferred system of the present invention includes a buffered aqueous salt solution. The salt concentration, determined using entire salt formula as opposed to a formula representing an ionized form of the salt, of the solution is at least about 3 molar, and is preferably in the range of about 3 to about 7 molar, and more preferably is in the range of about 4 to about 6 molar.

Preferred salts are those that upon dissolution in $CO_2$-free distilled water provide a pH value of about 6.5 to about 7.8, i.e., neutral salts such as NaCl, LiCl, KCl and the like. In another preferred embodiment, the salt is chaotropic and has an anion such as perchlorate, iodide, thiocyanate, acetate, trichloroacetate, hexafluorosilicate, tetrafluoroborate and the like. Preferred cations for a chaotropic salt are provided by the elements lithium, sodium, potassium, cesium, rubidium, guanidine and the like. More than one salt can be present in the buffered aqueous salt solution, a preferred combination of salts being NaI/KBr, preferably with the ratio of NaI to KBr such that the salt solution does not promote dissolution of agarose gels.

As previously discussed, it has now been discovered that one of the problems associated with previously known methods for isolating nucleic acids by adsorption to a silica matrix was failure to maintain a pH value that mediates binding, i.e., a pH value in the range of 7 to 8, preferably 7.2–7.8, for DNA and 4 to 6 for RNA. The solution provided by the present invention is in providing of an aqueous salt solution that has sufficient buffering capacity so that when it is admixed with a nucleic acid-containing sample the pH value of the admixture formed favors binding of either RNA or DNA, but not a significant amount of both.

Thus, an aqueous buffered salt solution of the present invention further contains at least one buffering agent and has a buffering agent concentration sufficient to provide a buffering capacity corresponding to that which 0.1 to 1 molar tris(hydroxymethyl)aminomethane or 0.1 to 1 molar sodium phosphate would provide in the solution, i.e., in a solution having the same salt at the same salt concentration. Tris(hydroxymethyl)aminomethane and sodium phosphate are preferred buffering agents, that when present at a concentration of about 0.1 to about 1 molar in the salt solution provide sufficient buffering capacity, in the pH value range of 4 to 6 for RNA and 7 to 8 for DNA, to maintain the desired pH values upon admixture with the nucleic acid-containing sample at a ratio of at least 2 volumes of buffered aqueous salt solution to 1 volume of nucleic acid-containing sample.

Buffering agents other than tris(hydroxymethyl) aminomethane can be used, but they must be present in the solution at a concentration that has the capacity to resist a change in pH value upon the addition of either H+ or OH– in a manner that is similar to that of 0.1 to 1 molar tris(hydroxymethyl)aminomethane or 0.1 to 1 molar phosphate ion. A combination of buffering agents can be used, so long as the solution has the required buffering capacity. Methods for determining the buffering capacity of a solution are well known in the art.

Of course, the comparison of buffering capacity is carried out in the presence of the salt to be used, at the salt concentration to be used, and with the solutions being compared at about the same temperature, preferably at a temperature within the range of about 15° C. to about 25° C. Other exemplary buffering agents include sodium acetate, and the like.

Preferred buffered aqueous salt solutions include the following:

Formula I: salt at a concentration in the range of 3 to 6 molar, 0.1 molar tris(hydroxymethyl) aminomethane, pH value range from about 7.1 to about 7.8;

Formula II: salt at a concentration in the range of 3 to 6 molar, about 0.6 to about 0.7 molar tris(hydroxymethyl)aminomethane, pH value range from about 7.1 to about 7.5; and Formula III: salt at a concentration of at least about 3 molar, 0.1 to about 1 molar tris(hydroxymethyl) aminomethane or 0.1 to about 1 molar sodium phosphate, pH value range from about 4 to about 6.

Preferably, the buffered aqueous salt solution is substantially free of cyclohexanediamine tetraacetate (CDTA), i.e., contains less than about 1 mM CDTA.

In one embodiment, the invention contemplates a system for media preparation that includes, in a package, a unit dose of a dry-concentrate of a culture medium capable of supporting growth of cells containing plasmid DNA. A dry concentrate of medium comprises the dry reagent components that make up a conventional growth medium, such as LB-broth and the like bacterial culture media. Exemplary media are described herein.

The term "unit dose" as it pertains to the media of the present invention refers to physically discrete units each suitable for providing, upon dissolution in a predetermined amount of water, such as about 50 to about 500 ml, preferably 50 ml, 100 ml, 150 ml, 200 ml and the like, a complete culture medium capable of supporting the growth of cells containing plasmid DNA. The specifications for the novel unit dose of a medium of this invention are dictated by and are directly dependent on (a) the unique characteristics of the nutrients and the particular nutrient requirements of the organism to be grown, and (b) the limitations inherent in the art of compounding such nutrients for use in culture media, as are disclosed in detail herein, these being features of the present invention.

The unit dose of dry-concentrate medium can be supplied in a variety of formats, including packaged in containers, pressed into tablets, and the like. Particularly preferred are gelatin capsule containers for ease of manipulation and ease of uniform dissolution of the concentrated medium.

The packaging for a unit dose form can vary widely. In one embodiment, the packaging is comprised of a dissolvable material, which can be either inert, inactive or nutritional, from the perspective of the nutrient medium the packaging contains. Preferably, the material is dissolvable in water or other aqueous solutions. The art of dissolvable packaging is well known and will not be recited here, but exemplary dissolvable materials include gelatin, polysaccharides, sugar, corn starch, short water-soluble inert polymers, binders, and the like, and combinations thereof.

A preferred system for isolating nucleic acids includes a unit dose form of the above dry-concentrate medium in a separate package to be used for the preparation of culture media for culturing cells or microorganisms for the preparation of a nucleic acid to be isolated according to the methods of the invention. Preferred are bacterial media such as L-broth and the like. Exemplary media are described herein.

Thus, particularly preferred systems further include a one or more unit dose capsules, containing an amount sufficient to prepare culture medium for growing at least one sample of microorganisms for the preparation of nucleic acids to be isolated by the present invention.

In another preferred embodiment, a system of this invention includes a sieve for separating insoluble globular protein from the supernatant formed upon centrifugation of a cell lysate. Preferably, the sieve has a mesh size in the range of 90 to 350, preferably 100 to 325, and more preferably 200, in U.S. Mesh Size American AMSI/ASTM Series units. It should be noted that the AMSI/ASTM Series mesh sizes 90, 200 and 325 correspond to aperture sizes of 160, 75 and 45 microns, respectively. The sieve has a diameter or long-axis of at least 1 inch and is preferably a square having sides of about 2 inches. Useful sieves can be prepared from commercially available materials such as screen made of monofilamentous nylon, polyfilamentous polyester and the like. An exemplary sieve was used herein to form the filtered solution as described in Example 2.

Still another preferred system further includes a filter for use in the filter-based separation step described in Examples 5 and 7 to accommodate an isolation method of this invention having a simplified wash and elution step. In that method, the filter is used to separate the glass particles from the various buffers during binding, wash and/or elution steps. A separation filter can be provided in a variety of formats depending upon the particular separation means being utilized so long as the filter has the capacity to retain the glass particle while allowing aqueous solutions to pass. For example, the separation means may be facilitated by pressurized liquid such as from a syringe as described in Example 5, or by gravity from centrifugation as described in Example 7.

The separation filter, in these embodiments has a pore size selected to retain the particulate glass yet allow the various buffers to conveniently pass. The pore size can be varied, and depends on the minimum diameter of the particulate glass to be filtered. Typical and preferred filters have a pore size of about 0.1 to 1.0 micrometers ("$\mu$" or microns), and preferably about $0.45\mu$.

Thus, in one embodiment, a separation filter for use in the present invention can be adapted for use in a pressurizable chamber adapted for attachment to a pressurized liquid supply, thereby allowing the delivery of the particulate glass suspension to the filter, together with any of the various buffers. The chamber contains an outlet after the filter for collecting the aqueous solution that passes the filter. An exemplary separation filter chamber is the syringe-mounted filter and system described in Example 5. Particularly preferred is a separation filter according to the design of the Gelman Acrodisc, and the like chamber-based filter units.

In another embodiment, a separation filter for use in the present invention can be adapted for use in a centrifugation step. Such filters are conveniently in the form of a centrifugation tube adapted to contain a separation filter with an upper chamber above the filter and a lower chamber below the filter. Typically, the tube's lower chamber is detachable from the filter to allow the removal of liquids from the lower chamber collected during centrifugation. Exemplary centrifugable separation filters are described in Example 7, and are available from a variety of commercial vendors, such as the SPIN-X centrifuge filter unit (COSTAR, Cambridge, Mass.) or the MC Filter Units from Millipore (Bedford, Mass.).

A preferred system of this invention further includes, in a separate container, plasmid DNA as a control. Any plasmid capable of production in eucaryotic or procaryotic culture is suitable, such plasmids being well known in the art and commercially available from many sources. Exemplary plasmids suitable for inclusion as a control or standard in a system of this invention include pUC18, pBR322, YEP24, YRP17, M13ampl8, bacteriophage X174 and the like. The plasmid can be provided in isolated form or in a host cell transformed therewith.

A preferred system of this invention further includes instruction for use of at least one of the system components.

"Instructions for use" typically include a tangible expression describing or identifying a system component or at least one parameter for using the system such as the relative amounts of the sample and component(s) to be admixed, maintenance time periods for component/sample admixtures, temperature and the like.

The packages and containers discussed herein in relation to systems are those customarily used in the chemical arts. Such packages and containers include glass and plastic (e.g., polyethylene, polypropylene and polycarbonate) bottles, vials, tubes, plastic and plastic-foil laminated envelopes and the like.

A preferred embodiment of a system of this invention includes a syringe and a filler adapted for attachment to the nozzle of the syringe. The pore size of the filter is sufficiently small to retain the particulate glass that forms a part of the system. The binding and elution processes described herein can be performed in the syringe using the filter attached thereto as a means for separating DNA-matrix complexes from solution and separating eluted DNA from glass particles.

In another embodiment, the system of the invention can further contain a centrifuge tube according to the present invention having a filter means for retaining particulate glass that allows the elution of aqueous solutions by centrifugal elution methods, as described herein.

B. Methods For Isolating Nucleic Acids

The present invention contemplates any method of isolating nucleic acid molecules using a system of this invention.

In one embodiment, a method of this invention is useful for isolating plasmid DNA from a sample containing the plasmid and other host-cell components such as chromosomal DNA, tRNA, mRNA, protein and the like. Preferably the sample is substantially free of cell-membranes or fragments thereof. The method includes the following steps:

a) A binding reaction admixture is formed by admixing the sample with an insoluble silica matrix, preferably particulate glass as described hereinbefore, and a before described buffered aqueous salt solution having a pH value of about 7 to about 8. The buffered salt solution includes, i) salt at a concentration of at least 3 molar, preferably in the range of about 4 to about 6 molar, and ii) a buffering agent at a concentration sufficient to provide a buffering capacity corresponding to that which 0.1 to 1 molar tris(hydroxymethyl)aminomethane or 0.1 to 1 molar phosphate ion would provide in the solution. Preferred buffered aqueous salt solutions are those corresponding to formulas I and II.

b) The binding reaction admixture is maintained for a predetermined time period sufficient for the plasmid DNA to bind to the silica matrix to form an insoluble DNA-matrix complex and a remaining admixture. The time period ranges from minute to hours, such as about 1 min to about 4 hours and is preferably in the range of 5 to 30 min.

c) The insoluble DNA-matrix complex is then separated from the remaining admixture to form isolated complex. Separation can be performed by any of the well known methods for partitioning an insoluble material from an aqueous solution. Preferred methods include centrifugation, filtration, gravimetric sedimentation and the like. In preferred embodiments, the complex is washed with a buffer (wash buffer) one to several times to insure removal of any residual remaining admixture, e.g., RNA, protein and the like.

d) The plasmid DNA is then recovered from the isolated DNA-matrix complex to form isolated plasmid DNA. Recovery is typically performed by elution with a low ionic buffer, e.g., 0 to 1M salt, preferably about 0 to 50 mM salt. A preferred elution buffer is distilled water.

The elution buffer can also be buffered such that it has a buffering capacity equivalent to about 1 to 100 mM Tris at a pH of about 6 to 8.

The concentration of the isolated plasmid DNA thus produced can be determined by methods well known in the art and adjusted, if necessary, by dilution or concentration by ethanol precipitation.

The above method can be adapted for the isolation of RNA by substituting a buffered aqueous salt solution according to formula III for that described in step a).

In another embodiment, the present invention contemplates a method for isolating DNA from an agarose gel sample containing the DNA. The method includes the following steps:

a) A gel-dissolving reaction admixture is formed by admixing the gel sample with a before described buffered aqueous chaotropic salt solution having a pH value of about 7 to about 8. The salt solution contains a chaotropic salt at a concentration of at least 3 molar, preferably about 4 to about 6 molar. In addition the salt solution includes a buffering agent at a concentration sufficient to provide a buffering capacity corresponding to that which 0.1 to 1 molar tris(hydroxymethyl) aminomethane or 0.1 to 1 molar phosphate ion would provide in the solution. Preferred buffered chaotropic salt solutions include those corresponding to formulas I and II.

b) The gel-dissolving reaction admixture is maintained at about 45 to about 65, preferably about 55 degrees C. for a predetermined time period sufficient for the gel sample to dissolve to form a dissolved sample.

c) The dissolved sample is admixed with an insoluble silica matrix, preferably particulate glass as described hereinbefore, to form a binding reaction admixture.

d) The binding reaction admixture is maintained for a predetermined period of time sufficient for the DNA present in the sample to bind to the matrix to form a solution containing dissolved agarose and an insoluble DNA-matrix complex. The period of time is similar to that previously described in step b) of the plasmid DNA isolation method.

e) The insoluble DNA-matrix complex is separated from the dissolved agarose to form an isolated DNA-matrix complex. This is accomplished in a manner similar to that described in step c) of the plasmid DNA isolation method.

f) The DNA is recovered from the isolated complex to form isolated DNA. This is accomplished in a manner similar to that described in step d) of the plasmid isolation method. In addition the DNA can be quantitated, concentrated or diluted as previously described.

The above method can be adapted to isolate RNA from an agarose gel using a buffer according to formula III wherein the salt is a chaotrope in place of the buffer described in step a).

EXAMPLES

The following examples are intended to illustrate, but not limit, the present invention. Accordingly, variations and equivalents, now known or later developed, that would be within the purview of one skilled in this art are to be considered to fall within the scope of this invention, which is limited only as set forth by the appended claims.

1. Preparation of Particulate Glass

Silica in the form of grade AH glass beads was obtained from Cal-Chem (San Diego, Calif.). The glass beads were suspended in 50% nitric acid and boiled for 1 hour. The beads were allowed to settle for one week without agitation and the excess liquid was decanted off of the settled bead layer. Thereafter the beads were washed 6 times by sequential cycles of a resuspension in water followed by a one week settling period through still water and decantation to form washed glass beads.

Size fractionation of the washed glass beads was accomplished by first mixing the washed glass beads into a suspension followed by maintaining the glass beads in a stationary cylindrical container over time to allow the beads (particles) to settle at unit gravity over a distance of 100 centimeters (cm). At any given time particles in suspension are referred to as fines and the settled particles form a layer at the bottom of the cylinder below the fines. Separation of the fines from the settled layer creates a population of glass particles that may be defined by the rate of sedimentation in centimeters per minute (cm/min) or defined by the time that the fines were removed after mixing.

Five minutes after a first mixing, the fines were removed from above the settled particle layer. The removed fines were then allowed to settle for an additional 20 minutes in a similar cylindrical container and the resulting fines were then removed from the resulting settled layer. The process was repeated and by this method, the above washed glass suspension was fractionated into samples of particulate glass that settled at various times as indicated in Table 1 below.

The resulting particulate glass fractions were analyzed by scanning electron microscopy to evaluate the characteristics of size and shape of the glass particles present in each fraction. Electron microscopy was conducted by MICRON, INC. (Wilmington; Del.), photographs were prepared and are shown in FIGS. 1 through 4. By comparison of the particles to the size marker in each sample, the range of sizes and average size were visually estimated for each sample and is reported in Table 1.

TABLE 1

| | Particulate Glass Fractions | | | |
|---|---|---|---|---|
| Fraction # | Sediment[a] Time | Sediment[b] Rate | Size Range | Avg. Size |
| 1 | 0–5 min | >20 | 15–50$\mu$[c] | 25$\mu$ |
| 2 | 5–20 min | 20–5 | nd | nd |
| 3 | 20 min–2 hrs | 5–.01 | nd | nd |
| 4 | 2 hrs–1 wk | .01–.008 | 1.5–20 | 8$\mu$ |
| 5 | 1 wk–6 wks | .008–.001 | 0.8—3$\mu$ | 2$\mu$ |
| 6 | 6 wks + | <.001 | 0.2–1$\mu$ | 0.5$\mu$ |

[a]Sediment time connotes that the fraction sedimented between the indicated times.
[b]Sediment rate is a measure in cm/min of the range of rates of sedimentation for particles in that fraction.
"$\mu$" means micrometers.

2. Isolation of DNA from Agarose Gels Using Particulate Glass

All DNA manipulations were done according to standard procedures. See Maniatis et al., *Molecular Cloning: A Laboratory Manual,* Cold Spring Harbor Laboratories, Cold Spring Harbor, N.Y., 1982.

Plasmid pUC18 DNA was prepared by techniques well known in the art and was then electrophoresed on a 1% agarose gel to deposit the plasmid into an agarose gel. The gel and its contents were then stained with ethidium bromide. Next the DNA sample in the gel was visualized by exposure to long-wave ultraviolet light. The gel was cut to isolate the agarose containing the band of visualized plasmid DNA. The agarose sample had a volume of about 0.5 ml and contained about 3 ug of plasmid DNA and was placed into a 1.5 microcentrifuge tube.

A solution of sodium iodide having a molarity of about 6 molar (M) was prepared by admixing 0.75 gm sodium bisulfite with 40 ml distilled water (dH2O) and 45 gms of sodium iodide. One ml of the sodium iodide solution was added to the microcentrifuge tube containing the agarose sample, and the tube was then maintained at 55° C. for about 5 minutes with a periodic agitation of the solution about every minute for about 5 seconds per agitation to allow the agarose to dissolve to form an agarose-plasmid DNA solution.

Five microliters ($\mu$l) of a suspension of particulate glass, prepared as in Example 1, obtained from a sample of either fraction 1, 4, 5, or 6 and each suspension having a concentration of about 50 percent (v/v) of glass per dH2O, were then admixed with the agarose DNA solution to form a binding reaction admixture. The admixture was then maintained for about 5 minutes at about 4° C. in an ice bucket with periodic agitation of the suspension about every minute for about 5 seconds for each agitation to allow the DNA present in the solution to form an insoluble DNA-particulate glass complex. The microcentrifuge tube was then centrifuged for 15 seconds at about 12,000×g and the resulting supernate was removed to form isolated DNA-matrix complex in a pellet.

About 200 $\mu$l of wash buffer (100 mn NaCl, 10 mM Tris, 1 mM EDTA, pH 7.5, 50% ethanol) was added to the DNA-glass pellet. The complex was resuspended by agitation and the suspension was centrifuged as before. The resulting pellet was recovered by removing the supernatant and this wash procedure was repeated twice to form an isolated complex. Five $\mu$l of dH2O was then added to the thrice washed isolated complex and maintained at 55° C. for about 5 minutes. The microcentrifuge tube containing the added dH2O and particulate glass was centrifuged at 12,000×g for about 15 seconds and the resulting supernate was recovered to form a first eluted DNA solution. Five ul of dH2O was again added to the glass pellet, the above maintenance at 55° C. and centrifugation steps repeated, and the supernate was recovered to form a second eluted DNA solution.

Figure 5:
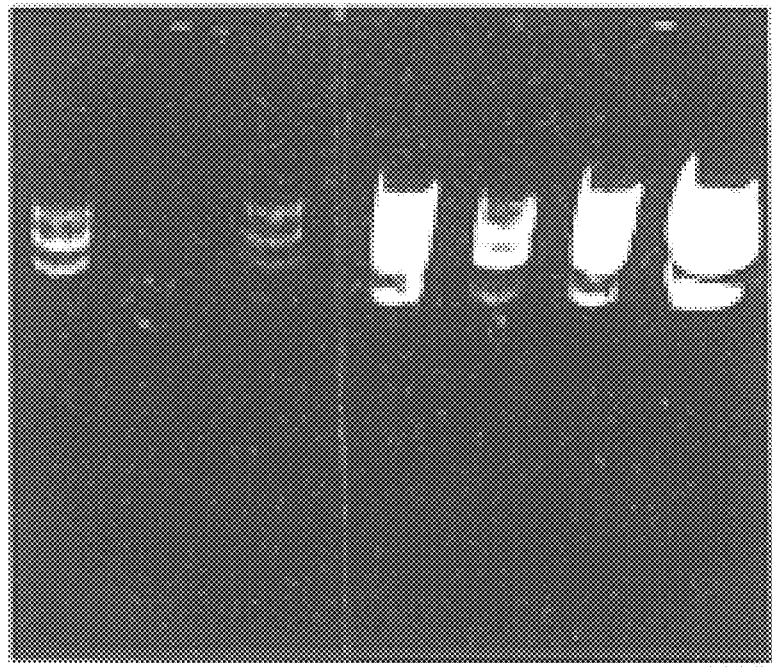
FIG. 5 illustrates the relative binding capacity of particulate glass fractions used to isolate DNA from agarose gels by the procedure described in Example 2. Plasmid DNA was isolated from an agarose gel using particulate glass fraction 4 (Lanes 1 and 4), fraction 5 (Lanes 3 and 6) or fraction 6 (Lanes 2 and 5) and analyzed by agarose gel electrophoresis. DNA isolated from the particulate glass after a first elution (Lanes 4–6) and after a second elution (Lanes 1–3) are shown. A sample of DNA was also analyzed (Lane 7) as a control that corresponds to the starting plasmid DNA in an amount equal to the amount present in each agarose sample before isolation.

The various first and second eluted DNA solutions, prepared using the different particulate glass fractions, were then applied to and electrophoresed on 1% agarose gels to evaluate the relative binding capacity of each particulate glass fraction prepared in Example 1. As shown in FIG. 5, plasmid DNA was recovered from agarose gel slices at efficiencies that depend upon the size fraction of the particulate glass. Fractions 8 and 10 exhibited the highest binding capacity. Comparison of the first and second elution of isolated DNA indicates that most of the isolated DNA was released by a first elution.

3. Preparation of Media in Unit Dose Formulation

Culture medium capable of supporting growth of the bacterial cell *Escherichia coli* (*E. coli*) containing plasmid DNA was prepared by first admixing 7 gms yeast extract, 14 gms bacto-tryptone, 1.25 gm sodium chloride (all from DIFCO Laboratories, Detroit, Mich.), 0.3 gm Tris Base and 1.6 gm Tris-HCl (both Tris reagents [tris(hydroxymethyl) aminomethane] were obtained from Sigma Chemical Co., St. Louis, Mo.) to form dry concentrate media powder, i.e., having less than 5% by weight, preferably less than 1% by weight, water.

A culture medium designated as LB-Medium (Luria-Bertani Medium) was also separately prepared by admixing 10 gm tryptone, 5 gm yeast extract, 10 gm sodium chloride, and a small amount of sodium hydroxide sufficient to form a medium having a pH of approximately 7.0 when reconstituted into a liquid medium. The powders are mixed, milled in a ball mill to a consistent 300 mesh size or smaller for admixture into a one liter medium formulation. The ingredients are available from a variety of sources such as DIFCO Laboratories, or BBL (Becton-Dickinson).

The resulting powder admixture was packaged into either a 00 or 000 size gelatin capsule using manual or automated capsule-filling machinery. A 00 size capsule will hold about 0.7 gm of LB medium, and a 000 capsule will hold about 1 gm of LB medium. Due to the hygroscopic nature of the media ingredients, it is important that the admixing of powdered reagents, and addition to capsules be conducted in an environment having relative humidity of less that 10%. To achieve this degree of humidity, it may be necessary to utilize air conditioners that are outfitted with dehumidifiers, and allow the dehumidifiers to form a relatively dry environment.

The media powder was packaged into unit dose amounts by placing 1 gm of the media powder into a size 00 clear gelatin capsule (CAPSUGEL, Warner Lambert, Greenwood, S.C.) to form media capsules. The media may alternatively contain binders for the powdered formulations.

Two media capsules were admixed with 50 milliliters (mls) distilled water (dH2O) and subjected to a standard autoclave procedure to sterilize the liquid admixture. After autoclaving and an additional time of about 15 minutes for the autoclaved admixture to reduce in temperature, ampicillin was added to a concentration of 50 micrograms (mg) per ml to form a unitary culture medium.

4. Isolation of Plasmid DNA from Bacterial Cells Using Particulate Glass

*E. Coli* bacteria strain DH1 containing plasmid pUC18 (obtainable from Bethesda Research Laboratories, Gaitherburg, Md.) were inoculated into the 50 mls of unitary culture medium prepared in Example 3 and the inoculated culture was maintained at 37° C. with moderate aeration for about 16 hours to form a saturated bacterial culture. The saturated culture was centrifuged at 8000×g for 5 minutes to pellet the bacterial cells, the pellet was recovered and excess medium removed. The approximate weight of the resulting cell pellet was determined to form a weighed cell pellet.

Prelysis buffer, which is included in preferred embodiments of the present invention, containing 50 mM Tris, 40 mM EDTA (ethylenediaminetetraacetic acid) and 50 mM glucose at a pH of about 8.5 was admixed with the weighed cell pellet at a ratio of 1 ml buffer per 0.5 gms of pellet. The pellet was resuspended in the prelysis buffer by agitation and the suspension was maintained at room temperature for 5 minutes. Thereafter, 2 mls of alkaline lysis buffer, which is included in preferred embodiments of this invention, containing 200 mM NaOH, and 1% SDS (sodium dodecyl sulfate) was admixed with the suspension, and the admixture was maintained for 5 minutes at room temperature with a continuous gentle agitation. Next, 1.5 mls of neutralizing solution which is included in preferred embodiments of this invention, prepared by admixing 40 mls of glacial acetic acid (99.5%) with 1 liter of 3M potassium acetate in water, was admixed with the lysed bacterial pellet suspension, and the resulting admixture was placed onto crushed ice (frozen water) and maintained for 10 minutes to form a neutralized solution.

The neutralized solution was centrifuged at 12,000×g for 15 minutes at 4° C. and the resulting supernatant was recovered. The recovered supernate was then poured through a nylon monofilament fabric having a mesh of about 200 and an aperture of about 75 microns between fibers (DA-KAR, San Diego, Calif.), and the liquid passing through was recovered to form a filtered solution. The volume of the filtered solution was determined, isopropanol was then admixed with the filtered solution in an amount equal to 0.6 volumes of the filtered solution and the resulting admixture was centrifuged at 8,000×g for 10 minutes at 4° C. The resulting precipitated cell lysate pellet was recovered by inverting the centrifuge tube, draining off excess supernate and adding 0.25 mls of TE buffer (10 mM Tris, 1 mM EDTA, pH 8.0) to form a dissolved pellet.

Binding buffer was prepared by first adding excess potassium bromide to a 1M Tris (pH 7.3) solution to form a saturated KBr solution at 25° C., and then admixing ⅓ volume of sodium iodide solution (prepared in Example 2) with ⅔ volume of the saturated KBr solution.

One ml of binding buffer was admixed with the dissolved pellet in a 1.5 ml microfuge tube, and 75 ml of a suspension of particulate glass, prepared as in Example 1 from fraction 4 and having a concentration of about 50% (v/v) of glass per $dH_2O$, were admixed to form a binding reaction admixture. The admixture was maintained at room temperature for 5 minutes with periodic agitation of the admixture about every minute for about 5 seconds per agitation to allow the plasmid DNA present in the admixture to bind to the particulate glass and form an insoluble DNA-matrix complex. Thereafter the admixture was centrifuged for 15 seconds at about 12,000×g to form a plasmid DNA-bound glass pellet. The DNA-bound glass pellet was washed three times with binding buffer and then washed three times using wash buffer as described in Example 2, and the bound plasmid DNA was eluted as in Example 2 except that 100 μl of dH2O was used to produce the first eluted DNA solution.

Isolated plasmid DNA present in the eluted DNA solution was analyzed for yield, purity and quality on agarose gels as described in Example 2. The results of that gel analysis show that the above procedure represents a method that produces plasmid DNA that is substantially free of RNA, and chromosomal DNA. However, numerous variations of salt concentration, choice of salt, pH, choice of buffer and buffer concentration were evaluated in the binding buffer (buffered aqueous salt solution) and also found to facilitate plasmid DNA isolation. Table 2 shows the results of the preferred binding buffer, in addition to showing the results when substituting a variant binding buffer that contains the salt and buffer conditions indicated in Table 2 in place of the binding buffer described in the text. In all cases, the buffer was prepared and the pH of the buffer was adjusted at room temperature before the salt was admixed to produce the final binding buffer. The concentrations indicated in Table 2 correspond to binding buffer before admixture with the dissolved pellet and particulate glass.

TABLE 2

Effects of Salt Selection, Salt Concentration and pH on Plasmid DNA Isolation Using Particulate Glass

| | | | | Binding Pattern[b] | |
| Salt[a] | Concentration | Buffer | pH | DNA | RNA |
| --- | --- | --- | --- | --- | --- |
| $NaIO_4$ | Sat.[c] | — | nd[d] | – | – |
| $NaBrO_4$ | Sat. | — | nd | – | – |
| NaBr | Sat. | — | nd | + | – |

TABLE 2-continued

Effects of Salt Selection, Salt Concentration and pH on Plasmid DNA Isolation Using Particulate Glass

| | | | | Binding Pattern[b] | |
| Salt[a] | Concentration | Buffer | pH | DNA | RNA |
| --- | --- | --- | --- | --- | --- |
| KBr | Sat. | — | nd | + | – |
| KBr | Sat. | — | nd | – | – |
| KBr | Sat. | — | nd | + | + |
| KBr | Sat. | — | nd | – | – |
| KBr | Sat. | 1M Tris | 6.0 | – | +++ |
| KBr | Sat. | 1M Tris | 7.0 | + | + |
| KBr | Sat. | 1M Tris | 7.2 | +++ | – |
| KBr | Sat. | 1M Tris | 7.5 | ++ | – |
| KBr | Sat. | 1M Tris | 7.8 | + | – |
| KBr | Sat. | 1M Tris | 8.0 | – | – |
| NaBr | Sat. | 1M Tris | 6.0 | – | +++ |
| NaBr | Sat. | 1M Tris | 7.0 | – | +++ |
| NaBr | Sat. | 1M Tris | 8.0 | – | – |
| NaI | 6M | 0.1M Tris | 7.4 | +++ | – |
| NaI | 6M | 0.1M Tris | 7.8 | ++ | – |
| NaI/KBr[e] | 2M/2.6M | .66M Tris | 7.3 | +++ | – |
| NaCl | 3M | 0.1M Tris | 7.2 | + | ++ |
| CsCl | 3M | 0.1M Tris | 7.2 | ++ | ++ |
| KI | 3M | 0.1M Tris | 7.2 | +++ | + |
| $NaClO_4$ | 3M | 0.1M Tris | 7.2 | ++ | ++ |
| GN HCl | 3M | 0.1M Tris | 7.2 | ++ | + |
| GN SCN | 3M | 0.1M Tris | 7.2 | +++ | ++ |

[a]"CN HCl" refers to guanidine hydrochloride, and "GN SCN" refers to guanidine thiocyanate.
[b]DNA and RNA binding patterns were determined by analyzing the material isolated as described in Example 4 by using agarose gel electrophoresis to visualize the relative amounts of DNA and RNA obtained. "+++" means the maximum amount observed in comparison to a control buffer, "++" means about 20–50 percent of control, "+" means about 20 percent or less visible material compared to control, and "–" means no visible material present on the gel. For DNA, the control buffer is binding buffer, and for RNA, the control buffer is 4M KBr and 1M Tris at pH 6.0.
[c]"Sat." means a saturated salt solution prepared as in Example 4.
[d]"nd" means not done.
[e]"NaI/KBr" indicates the binding buffer described in the text of Example 4 that contains both salts, each at the concentration indicated.

Table 2 indicates that DNA isolation free of RNA can be conducted by using a binding buffer having a pH value over a specific pH range of about 7.2 to 7.5 for KBr and at least about 7.4 to 7.8 for NaI. Further, the combination of KBr and NaI, each at a concentration lower than 3M, was observed to produce maximal plasmid isolation free of RNA, whereas KBr alone at 3M did not produce satisfactory yields.

5. Particulate Glass Isolation of DNA Using a Filter-Based Separation Step

The above methods for isolating DNA from agarose in Example 2 or isolating plasmid DNA from bacterial cultures in Example 4 was modified to accommodate a procedure having simplified wash and elution steps. In that modified procedure, a filtration step was used to separate the particulate glass from the various buffers in place of a centrifugation step. This modified procedure was the same as in Example 2 or Example 4 except for the substitution of the centrifugation steps with the following separation steps as noted.

The dissolved pellet prepared in Example 4 was first admixed with the binding buffer to form a pellet binding solution. The solution was then drawn into a plastic 3 ml syringe that had fitted on its inlet a 0.45 micron (μ) filter (Gelman Acrodisc, Ann Arbor, Ill.), i.e., a syringe-mounted filter. The syringe also contained 100 ul of the particulate glass suspension in the barrel portion of the syringe such that by drawing up the pellet binding solution there was an admixing of the solution with the particulate glass suspension to form a binding reaction admixture in the syringe barrel. The reaction admixture was then maintained as before, and then the solution in the syringe was expelled to separate that solution from the retained insoluble DNA-matrix complex. In a similar manner, washes and elution were performed by drawing up the respective wash and elution buffers as described in Example 4. The eluted sample was collected as it was expelled from the outlet of the syringe-mounted filter. When this eluted sample was analyzed on agarose gels for plasmid DNA it was found to be comparable in yield and purity to the isolated DNA described in Example 4.

6. Particulate Glass Isolation of DNA Using a Sedimentation Based Separation Step The above methods for isolating DNA may be modified to accommodate wash and elution steps based on sedimentation at unit gravity as a means for separation in place of centrifugation. This modified procedure is conducted in the same manner as described in Example 2 or Example 4 except that the described centrifugation steps are substituted with the following sedimentation-based separation steps as noted.

The dissolved pellet prepared in Example 4 is added to a well of a microtiter plate and admixed therein with the binding buffer and the suspension of particulate glass as in Example 4 to form a binding reaction admixture.

The fraction of particulate glass used for a sedimentation-based separation is a fraction prepared as in Example 1 except that is it fractionated such that more than 98% of the glass particles in the fraction sediment under unit gravity over a 1 cm vertical distance in a time period between 15 seconds and 2 hours. For the purpose of saving time between washes, it is preferred if the sedimentation time occurs between 2 and 6 minutes.

The reaction admixture in the microtiter wells is maintained as in Example 4. Thereafter, in place of centrifugation the plates are held stationary and the particulate glass is allowed to settle. The liquid layer present above the settled glass is decanted (separated) and wash buffer is then admixed with the settled glass present in the microtiter well. Settling, separating and further admixing steps are then performed in this sedimentation-based mode to subject the glass particles to washes and elution essentially as described in Example 4 thus carried out to conduct the to yield isolated DNA in the first separated elutant solution.

7. Particulate Glass Isolation of DNA Using a Centrifugation Based Separation Step The above methods for isolating nucleic acids was modified to accommodate a procedure having simplified binding, wash and elution steps. In the present modified procedure, a centrifugal filtration step was used to separate the particulate glass from the various buffers in place of a centrifugation/decanting step, or the simple pressure filtration step described in Example 5. This modified procedure was generally the same as in Example 2 or Example 4 with the following exceptions to the steps for separating the particulate glass from any of the various buffers as noted.

As before, a solution containing nucleic acid is admixed with binding buffer and the particulate glass to form a binding reaction admixture, and the admixture was maintained as before to allow the formation of an insoluble DNA-matrix complex. Thereafter, the admixture was placed into the upper chamber of a SPIN-X centrifugal filtration unit (COSTAR, Cambridge, Mass.) and centrifuged on a microfuge apparatus for 15 seconds at about 12,000×g to force the liquid phase of the admixture through the filter into the lower chamber of the unit. The particulate glass bound nucleic acid molecules remain in the upper chamber of the filter unit. Thereafter, the particulate glass is washed three times with binding buffer and three times with wash buffer as described before, except at each wash, the liquid is removed by a centrifugation step to pass the liquid through the filter. The lower chamber was emptied as needed to allow for the repeated washes. Finally, the bound nucleic acids were eluted by the addition of elution buffer to the particulate glass as described before, except that the elution buffer was added to the upper chamber, and the unit was centrifuged to pass the elution buffer and eluted nucleic acids into the lower chamber where it was collected, thereby separating the nucleic acid from the particulate glass.

The use of the centrifugal filtration procedure yielded nucleic acid of similar purity as described before by the present methods. However, the resulting nucleic acids, when high molecular weight DNA was isolated by the present method, provides material that is less sheared (broken) than DNA isolated by multiple binding, washing and eluting steps that require resuspension and pipetting manipulations. Thus, the centrifugal filtration method yields superior high molecular weight DNA.

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. A composition for isolating nucleic acid molecules consisting essentially of particulate glass having a sedimentation time through 100 centimeters (cm) of still water at unit gravity in the range of 6 weeks to 20 minutes.

2. The composition of claim 1 wherein said sedimentation time is in the range of 6 weeks to 2 hours.

3. The composition of claim 1 wherein said sedimentation time is in the range of 1 week to 2 hours.

4. The composition of claim 1 wherein said sedimentation time is in the range of 6 weeks to 1 week.

5. A kit for isolating nucleic acid molecules comprising a composition consisting essentially of particulate glass having a sedimentation time through 100 centimeters (cm) of still water at unit gravity in the range of 6 weeks to 20 minutes, said kit further containing instructions for use of said composition for isolating said nucleic acid molecules.

6. The kit of claim 5 wherein said sedimentation time is in the range of 6 weeks to 2 hours.

7. The kit of claim 5 wherein said sedimentation time is in the range of 1 week to 2 hours.

8. The kit of claim 5 wherein said sedimentation time is in the range of 6 weeks to 1 week.

9. The kit of claim 5 further containing a filtration means having a pore size that retains the particulate glass and passes solutions.

10. The kit of claim wherein said pore size is 0.1 to 1.0 micrometers.

11. The kit of claim 9 wherein said filtration means is a filter in a pressurizable chamber having an inlet before the filter for delivery of liquid and an outlet after the filter for collecting liquid that passes the filter.

12. The kit of claim 9 wherein said filtration means is a filter in a centrifuge tube having an upper chamber above the filter and a lower chamber below the filter for collecting liquid that passes the filter.

13. The kit of claim 12 wherein said lower chamber is detachable from the filter to allow removal of the collected liquid from the lower chamber.

14. The kit of claim 5 further containing, in a separate package, a unit dose of a dry-concentrate of a culture medium capable of supporting growth of cells containing plasmid DNA.

15. The kit of claim 14 wherein said medium is in tablet or capsular form.

16. The kit of claim 14 wherein said unit dose packaging is dissolvable.

17. The kit of claim 14 wherein said dry medium has less than 5% water by weight.

18. The kit of claim 14 wherein said dry medium has less than 1% water by weight.

* * * * *